(12) United States Patent
Glukhovsky et al.

(10) Patent No.: US 7,753,842 B2
(45) Date of Patent: Jul. 13, 2010

(54) IN VIVO IMAGING DEVICE WITH A SMALL CROSS SECTIONAL AREA

(75) Inventors: Arkady Glukhovsky, Santa Clarita, CA (US); Gavriel Meron, Petach Tikva (IL)

(73) Assignee: Given Imaging Ltd., Yoqneam (IL)

( * ) Notice: Subject to any disclaimer, the term of this patent is extended or adjusted under 35 U.S.C. 154(b) by 243 days.

(21) Appl. No.: 11/892,815

(22) Filed: Aug. 27, 2007

(65) Prior Publication Data
US 2008/0200757 A1 Aug. 21, 2008

Related U.S. Application Data

(63) Continuation of application No. 10/482,218, filed as application No. PCT/IL02/00526 on Jun. 27, 2002, now abandoned.

(60) Provisional application No. 60/301,141, filed on Jun. 28, 2001.

(51) Int. Cl.
*A61B 1/05* (2006.01)
(52) U.S. Cl. .................. 600/130; 600/109; 600/160
(58) Field of Classification Search .......... 600/109, 600/129, 160, 101, 476, 130, 170, 171, 302; 348/76
See application file for complete search history.

(56) References Cited

U.S. PATENT DOCUMENTS

| | | | |
|---|---|---|---|
| 3,683,389 A | 8/1972 | Hollis | |
| 3,888,237 A | 6/1975 | Mori | |
| 3,971,362 A | 7/1976 | Pope et al. | |
| 4,217,045 A | 8/1980 | Ziskind | |
| 4,253,447 A | 3/1981 | Moore et al. | |
| 4,278,077 A | 7/1981 | Mizumoto | |
| 4,425,117 A | 1/1984 | Hugemann et al. | |
| 4,467,361 A | 8/1984 | Ohno et al. | |
| 4,622,954 A | 11/1986 | Arakawa et al. | |
| 4,689,621 A | 8/1987 | Kleinberg | |
| 4,692,608 A | 9/1987 | Cooper et al. | |
| 4,710,807 A | 12/1987 | Chikama et al. | |

(Continued)

FOREIGN PATENT DOCUMENTS

DE        34 40 177        5/1986

(Continued)

OTHER PUBLICATIONS

Japanese Office Action of Application No. JP 2003-509753 dated Aug. 16, 2007.

(Continued)

*Primary Examiner*—John P Leubecker
(74) *Attorney, Agent, or Firm*—Pearl Cohen Zedek Latzer, LLP

(57) ABSTRACT

An in vivo imaging device may include a capsule shaped housing and an image sensor. The capsule shaped housing may have a longitudinal axis and a window. The image sensor (e.g., a CMOS sensor) may include a pixel array portion and a circuitry portion. The circuitry portion may be segregated, for example longitudinally, from the pixel array portion. The pixel array portion may be disposed within said housing substantially parallel to said longitudinal axis.

A light deflecting element disposed at an angle smaller than 45 degrees with respect to the pixel array portion introduces image distortion which is compensated by a distortion compensation mechanism.

11 Claims, 5 Drawing Sheets

U.S. PATENT DOCUMENTS

| | | | |
|---|---|---|---|
| 4,741,327 A | 5/1988 | Yabe | |
| 4,809,680 A | 3/1989 | Yabe et al. | |
| 4,832,003 A | 5/1989 | Yabe | |
| 4,844,076 A | 7/1989 | Lesho et al. | |
| 4,857,724 A | 8/1989 | Snoeren et al. | |
| 4,858,002 A | 8/1989 | Zobel et al. | |
| 4,882,619 A | 11/1989 | Hasegawa et al. | |
| 4,890,159 A | 12/1989 | Ogiu | |
| 4,915,113 A | 4/1990 | Holman | |
| 4,918,521 A | 4/1990 | Yabe et al. | |
| 4,986,642 A | 1/1991 | Yokota et al. | |
| 5,108,407 A | 4/1992 | Geremia et al. | |
| 5,184,223 A | 2/1993 | Mihara et al. | |
| 5,191,879 A | 3/1993 | Krauter | |
| 5,216,512 A | 6/1993 | Bruijns et al. | |
| 5,279,607 A | 1/1994 | Schentag et al. | |
| 5,381,784 A * | 1/1995 | Adair | 600/166 |
| 5,421,337 A | 6/1995 | Richards-Kortum et al. | |
| 5,444,574 A | 8/1995 | Ono et al. | |
| 5,450,243 A | 9/1995 | Nishioka et al. | |
| 5,494,483 A | 2/1996 | Adair et al. | |
| 5,547,455 A | 8/1996 | McKenna et al. | |
| 5,598,205 A | 1/1997 | Nishioka et al. | |
| 5,603,687 A | 2/1997 | Hori et al. | |
| 5,604,531 A * | 2/1997 | Iddan et al. | 348/76 |
| 5,723,844 A | 3/1998 | Dow et al. | |
| 5,734,418 A | 3/1998 | Danna | |
| 5,776,050 A | 7/1998 | Chen et al. | |
| 5,782,771 A | 7/1998 | Hussman | |
| 5,797,837 A * | 8/1998 | Minami | 600/109 |
| 5,819,736 A | 10/1998 | Avny et al. | |
| 5,833,603 A | 11/1998 | Kovacs et al. | |
| 5,853,005 A | 12/1998 | Scanlon | |
| 5,904,647 A | 5/1999 | Ouchi | |
| 5,905,597 A | 5/1999 | Mizouchi et al. | |
| 5,929,901 A * | 7/1999 | Adair et al. | 348/76 |
| 5,938,585 A | 8/1999 | Donofrio | |
| 5,940,126 A | 8/1999 | Kimura et al. | |
| 5,980,453 A | 11/1999 | Forkey et al. | |
| 5,986,693 A * | 11/1999 | Adair et al. | 348/76 |
| 5,993,378 A | 11/1999 | Lemelson | |
| 5,999,844 A | 12/1999 | Gombrich et al. | |
| 6,010,453 A | 1/2000 | Fiddian-Green | |
| 6,019,721 A | 2/2000 | Holmes et al. | |
| 6,034,823 A * | 3/2000 | Togino | 359/629 |
| 6,043,839 A * | 3/2000 | Adair et al. | 348/76 |
| 6,074,349 A | 6/2000 | Crowley | |
| 6,100,920 A | 8/2000 | Miller et al. | |
| 6,142,930 A | 11/2000 | Ito et al. | |
| 6,165,128 A | 12/2000 | Cespedes et al. | |
| 6,204,524 B1 | 3/2001 | Rhodes | |
| 6,206,825 B1 | 3/2001 | Tsuyuki et al. | |
| 6,222,620 B1 | 4/2001 | Jung et al. | |
| 6,240,312 B1 | 5/2001 | Alfano et al. | |
| 6,266,550 B1 | 7/2001 | Selmon et al. | |
| 6,281,506 B1 | 8/2001 | Fujita et al. | |
| 6,285,897 B1 | 9/2001 | Kilcoyne et al. | |
| 6,458,074 B1 | 10/2002 | Matsui et al. | |
| 6,475,145 B1 | 11/2002 | Baylor | |
| 6,490,490 B1 | 12/2002 | Uchikubo et al. | |
| 6,527,753 B2 | 3/2003 | Sekine et al. | |
| 6,549,796 B2 | 4/2003 | Sohrab | |
| 6,579,311 B1 | 6/2003 | Makower | |
| 6,612,982 B1 | 9/2003 | Ouchi | |
| 6,632,175 B1 | 10/2003 | Marshall | |
| 6,648,814 B2 | 11/2003 | Kim et al. | |
| 6,659,940 B2 | 12/2003 | Adler et al. | |
| 6,692,432 B1 | 2/2004 | Yarush et al. | |
| 6,709,387 B1 | 3/2004 | Glukhovsky et al. | |
| 6,719,684 B2 | 4/2004 | Kim et al. | |
| 6,951,536 B2 | 10/2005 | Yokoi et al. | |
| 7,009,634 B2 | 3/2006 | Iddan et al. | |
| 7,044,908 B1 | 5/2006 | Montalbo et al. | |
| 7,122,001 B2 | 10/2006 | Uchiyama et al. | |
| 7,160,258 B2 | 1/2007 | Imran et al. | |
| 7,241,262 B2 | 7/2007 | Adler et al. | |
| 7,261,728 B2 | 8/2007 | Long et al. | |
| 2001/0035902 A1 | 11/2001 | Iddan et al. | |
| 2001/0040211 A1 | 11/2001 | Nagaoka et al. | |
| 2001/0049497 A1 | 12/2001 | Kalloo et al. | |
| 2001/0051766 A1 | 12/2001 | Gazdzinski | |
| 2002/0042562 A1 | 4/2002 | Meron et al. | |
| 2002/0103417 A1 | 8/2002 | Gazdzinski | |
| 2002/0109774 A1 * | 8/2002 | Meron et al. | 348/74 |
| 2002/0138009 A1 | 9/2002 | Brockway et al. | |
| 2002/0156347 A1 | 10/2002 | Kim et al. | |
| 2002/0165589 A1 | 11/2002 | Imran et al. | |
| 2003/0013370 A1 | 1/2003 | Glukhovsky | |
| 2003/0020810 A1 | 1/2003 | Takizawa et al. | |
| 2003/0023150 A1 | 1/2003 | Yokai et al. | |
| 2003/0092964 A1 | 5/2003 | Kim et al. | |
| 2003/0117491 A1 | 6/2003 | Avni et al. | |
| 2003/0130562 A1 | 7/2003 | Barbato et al. | |
| 2003/0167000 A1 | 9/2003 | Mullick et al. | |
| 2003/0174409 A1 | 9/2003 | Nagaoka et al. | |
| 2003/0214726 A1 | 11/2003 | Mihara | |
| 2004/0073087 A1 | 4/2004 | Glukhovsky et al. | |
| 2004/0092825 A1 | 5/2004 | Madar et al. | |
| 2004/0097791 A1 | 5/2004 | Tokuda et al. | |
| 2004/0133076 A1 | 7/2004 | Kobayashi et al. | |
| 2004/0153008 A1 | 8/2004 | Sharf et al. | |
| 2004/0176664 A1 | 9/2004 | Iddan | |
| 2004/0225189 A1 | 11/2004 | Kimoto et al. | |
| 2005/0143624 A1 | 6/2005 | Iddan | |
| 2006/0004255 A1 | 1/2006 | Iddan et al. | |
| 2006/0167339 A1 | 7/2006 | Gilad et al. | |
| 2007/0270651 A1 | 11/2007 | Gilad et al. | |

FOREIGN PATENT DOCUMENTS

| | | |
|---|---|---|
| EP | 0967656 A2 | 12/1999 |
| JP | 57-45833 | 3/1982 |
| JP | 59129819 | 7/1984 |
| JP | 61059308 | 3/1986 |
| JP | 63-070820 | 3/1988 |
| JP | 63-226615 | 9/1988 |
| JP | 2036835 | 2/1990 |
| JP | 3-289779 | 12/1991 |
| JP | 4109927 | 4/1992 |
| JP | 1992-144533 | 5/1992 |
| JP | 4-180736 | 6/1992 |
| JP | 5015515 | 1/1993 |
| JP | 06-114036 | 4/1994 |
| JP | 6142081 | 5/1994 |
| JP | 7289504 | 11/1995 |
| JP | 09327447 A | 12/1997 |
| JP | 10-65131 | 3/1998 |
| JP | 11326786 | 11/1999 |
| JP | 2001-112740 | 4/2001 |
| JP | 2001-170002 | 6/2001 |
| JP | 2001224553 | 8/2001 |
| WO | WO 92/21307 | 12/1992 |
| WO | WO 98/11816 | 3/1998 |
| WO | WO 01/08548 | 2/2001 |
| WO | WO 01/50941 | 7/2001 |
| WO | WO 01/53792 | 7/2001 |
| WO | WO 01/65995 | 9/2001 |
| WO | WO 01/87377 | 11/2001 |
| WO | WO 02/26103 | 4/2002 |
| WO | WO 03/090618 | 11/2003 |
| WO | WO 2004/028336 | 4/2004 |

| | | |
|---|---|---|
| WO | WO 2004/058041 | 7/2004 |

OTHER PUBLICATIONS

Japanese Office Action of Application No. JP 2003-509753 dated Feb. 23, 2009.
Office Action of Japan Application No. 2003-509753 dated May 26, 2008.
Office Action, issued Feb. 1, 2010, in connection with U.S. Appl. No. 11/025,124, filed Dec. 30, 2004.
U.S. Appl. No. 60/801,387, filed May 19, 2006, Swain et al.
U.S. Appl. No. 11/802,121, filed May 21, 2007, Gilad et al.
U.S. Appl. No. 60/801,385, filed May 19, 2008, Gilad et al.
U.S. Appl. No. 12/159,745, filed Dec. 22, 2008, Betesh, Ido.
International Search Report for PCT/IL2003/001104 dated Oct. 1, 2004.
The Radio Pill, Rowlands, et al., British Communications and Electronics, Aug. 1960, pp. 598-601.
"Video Camera to TAKE"—RF Systems Lab.
Wellesley company sends body montiors into space—Crum, Apr. 1998.
Wireless transmission of a color television moving image from the stomach using a miniature CCD camera, light source and microwave transmitter. Swain CP, Gong F, Mills TN. Gastrointest Endosc 1997;45:AB40.
PCT International Search Report of International Application No. PCT/IL01/00912, dated Jun. 15, 2003.
BBC News Online—Pill camera to 'broadcast from the gut', Feb. 21, 2000, www.news.bbc.co.uk.
Office Action issued on Jul. 1, 2009 in U.S. Appl. No. 10/540,890.
Office Action for U.S. Appl. No. 09/963,950, dated Jan. 26, 2005.
Office Action for U.S. Appl. No. 09/963,950, dated Sep. 29, 2003.
Office Action for U.S. Appl. No. 09/963,950, dated Oct. 22, 2003.
Final Office Action for U.S. Appl. No. 09/963,950, dated Apr. 8, 2004.
Search Report of European Application No. 02743598.1, dated Nov. 13, 2009.
Office Action for U.S. Appl. No. 11/025,124, dated Feb. 20, 2009.
Final Office Action for U.S. Appl. No. 11/025,124, dated Aug. 28, 2009.
Office Action, issued Jan. 4, 2006, in U.S. Appl. No. 10/683,344.
Office Action, issued Apr. 18, 2006, in U.S. Appl. No. 10/683,344.
Final Office Action, issued Oct. 30, 2006, in U.S. Appl. No. 10/683,344.
Notice of Allowance, issued Apr. 17, 2007, in U.S. Appl. No. 10/683,344.
Office Action, issued Dec. 17, 2002, in U.S. Appl. No. 09/826,163.
Office Action, issued Mar. 6, 2003, in U.S. Appl. No. 09/826,163.
Notice of Allowance, issued Jun. 23, 2003, in U.S. Appl. No. 09/826,163.

* cited by examiner

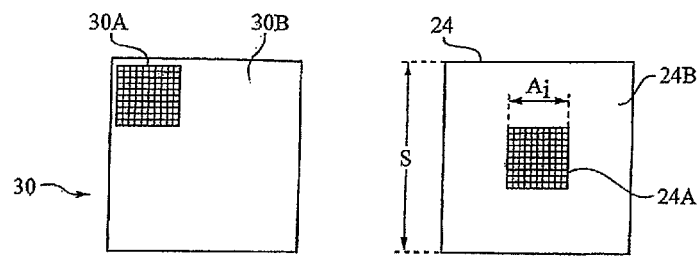
FIG. 2
PRIOR ART
FIG. 3
PRIOR ART
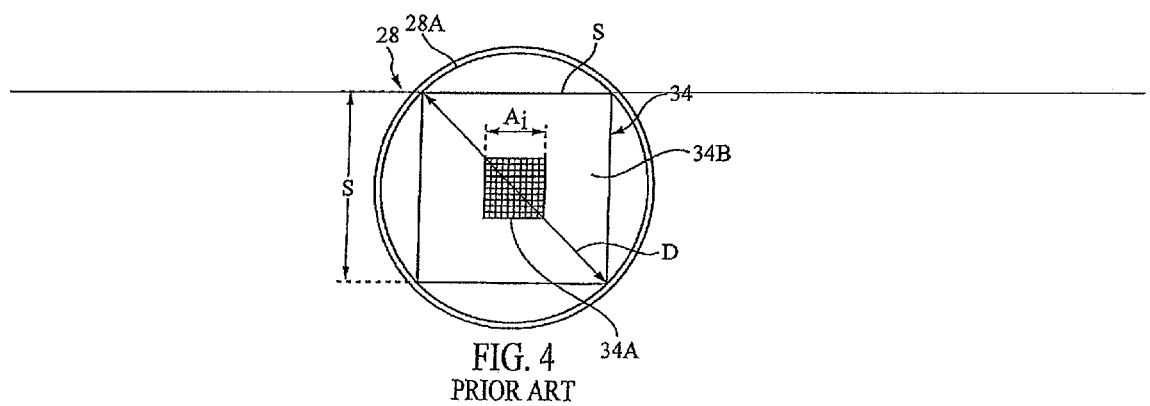
FIG. 4
PRIOR ART
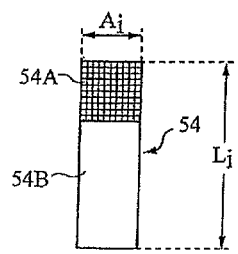
FIG. 5

IN VIVO IMAGING DEVICE WITH A SMALL CROSS SECTIONAL AREA

CROSS-REFERENCE TO RELATED APPLICATIONS

This application is a continuation of U.S. patent application Ser. No. 10/482,218, now abandoned, which was filed Dec. 29, 2003, as a National Phase Application of PCT International Application No. PCT/IL02/00526, International Filing Date Jun. 27, 2002, which claims priority of U.S. Provisional Patent Application No. 60/301,141, filed Jun. 28, 2001, all of which are incorporated herein by reference in their entireties.

BACKGROUND OF THE INVENTION

Devices and methods for performing in-vivo imaging of passages or cavities within a body are known in the art. Such devices may include, inter alia, various endoscopic imaging systems and devices for performing imaging in various internal body cavities.

Reference is now made to FIG. 1 which is a schematic diagram illustrating an embodiment of an autonomous in-vivo imaging device. The device 10A typically includes a capsule-like housing 18 having a wall 18A. The device 10A has an optical window 21 and an imaging system for obtaining images from inside a body cavity or lumen, such as the GI tract. The imaging system may include an illumination unit 23. The illumination unit 23 may include one or more light sources 23A. The one or more right sources 23A may be a white light emitting diode (LED), or any other suitable light source, known in the art, The imaging system of the device 10A may include an imager 24, such as a CMOS or CCD, which acquires the images and an optical system 22 which focuses the images onto the imager 24. Typically, the imager 24 is arranged so that it's surface 27 is perpendicular to the longitudinal axis 19 of the device 10A. The illumination unit 23 illuminates the inner portions of the body lumen through an optical window 21. Device 10A further includes a transmitter 26 and an antenna 27 for transmitting the image signal of the imager 24, and one or more power sources 25. The power source(s) 26 may be any suitable power sources such as but not limited to silver oxide batteries, lithium batteries, or other electrochemical cells having a high energy density, or the like. The power source(s) 25 may provide power to the electrical elements of the device 10A.

Typically, in the gastrointestinal application, as the device 10A is transported through the gastrointestinal (GI) tract, the imager, such as but not limited to a multi-pixel CMOS imager acquires images (frames) which are processed and transmitted to an external receiver/recorder (not shown) worn by the patient for recording and storage. The recorded data may then be downloaded from the receiver/recorder to a computer or workstation (not shown) for display and analysis. During the movement of the device 10A through the GI tract, the imager may acquire frames at a fixed or at a variable frame acquisition rate. For example, in one embodiment the imager (such as, but not limited to a CMOS imager) may acquire images at a fixed rate of two frames per second (2 Hz). However, other different frame rates may also be used, depending, inter alia, on the type and characteristics of the specific imager or camera or sensor array implementation which is used, and on the available transmission bandwidth of the transmitter 26. The downloaded images may be displayed by the workstation by replaying them at a desired frame rate. This way, the expert or physician examining the data is provided with a movie-like video playback which may enable the physician to review the passage of the device through the GI tact.

It may generally be desirable to decrease the size and particularly the cross sectional area of in vivo imaging devices, such as the device 10A of FIG. 1, or of imaging devices that are to be inserted into working channels of endoscope-like devices, or integrated into catheter-like devices which may be used in conjunction with guide wires, or the like. Smaller catheter like devices with reduced area may be inserted into narrower body cavities or lumens, such as for example, the coronary arteries, the urethra, the common bile duct, or the like and may also be easier to insert into working channels of other devices such as endoscopes, laparoscopes, gastroscopes, or the like.

Decreasing the cross-sectional area of such devices may be limited by the cross-sectional area of the imaging sensor, such as for example the imager 24 of FIG. 1

SUMMARY OF THE INVENTION

In one embodiment, an image sensor (e.g., a CMOS sensor) includes a pixel array portion and a circuitry portion, where the circuitry portion may be segregated, for example longitudinally, from the pixel array portion.

BRIEF DESCRIPTION OF THE DRAWINGS

The invention is herein described, by way of example only, with reference to the accompanying drawings, in which like components are designated by like reference numerals, wherein:

FIG. 2 is a schematic front view of the surface layout of a typical prior art CMOS imager.

FIG. 3 is a schematic front view of the imager 24 of FIG. 1;

FIG. 4 is a schematic cross sectional view illustrating a CMOS imager having a square cross-sectional area disposed within a housing having a circular cross-section;

FIG. 5 is a schematic top view showing the layout of a rectangular CMOS imager having segregated pixel array area and support circuitry areas, in accordance with a preferred embodiment of the present invention;

DETAILED DESCRIPTION OF THE INVENTION

In the following description, various aspects of the present invention will be described. For purposes of explanation, specific configurations and details are set s forth in order to provide a thorough understanding of the present invention. However, it will also be apparent to one skilled in be art that the present invention may be practiced without the specific details presented herein. Furthermore, well known features may be omitted or simplified in order not to obscure the present invention.

The present invention is based on providing an imager having a small cross-sectional area for implementing in vivo imaging devices such as, but not limited to, swallowable autonomous in-vivo imaging devices (capsule-like or shaped otherwise), and wired or wireless imaging units which are integrated into endoscope-like devices, catheter-like devices, or any other type of in-vivo imaging device that can be introduced into a body cavity or a body lumen.

It is noted that while the embodiments of the invention shown hereinbelow are adapted for imaging of the gastrointestinal (GI) tract, the devices and methods disclosed may be adapted for imaging other body cavities or spaces.

FIG. 2 is a schematic front view of the surface layout of a typical prior art CMOS imager. The CMOS imager 30 is an integrated circuit, which is typically implemented on a silicon wafer. The CMOS imager 30 includes an imaging sensor part 30A which is usually located at one of the corners of the frontal surface of the CMOS imager 30. The imaging sensor part 30A may include the two dimensional array of light sensitive diodes (not shown in detail) comprising the sensor pixels (not shown in detail), and may also include integrated amplification circuitry (not shown) and switching circuitry (not shown) for controlling the pixel sampling or readout, and may also include electrical con ducting paths for connecting the pixels to the functional units that perform the readout of the pixels.

Figure 1:
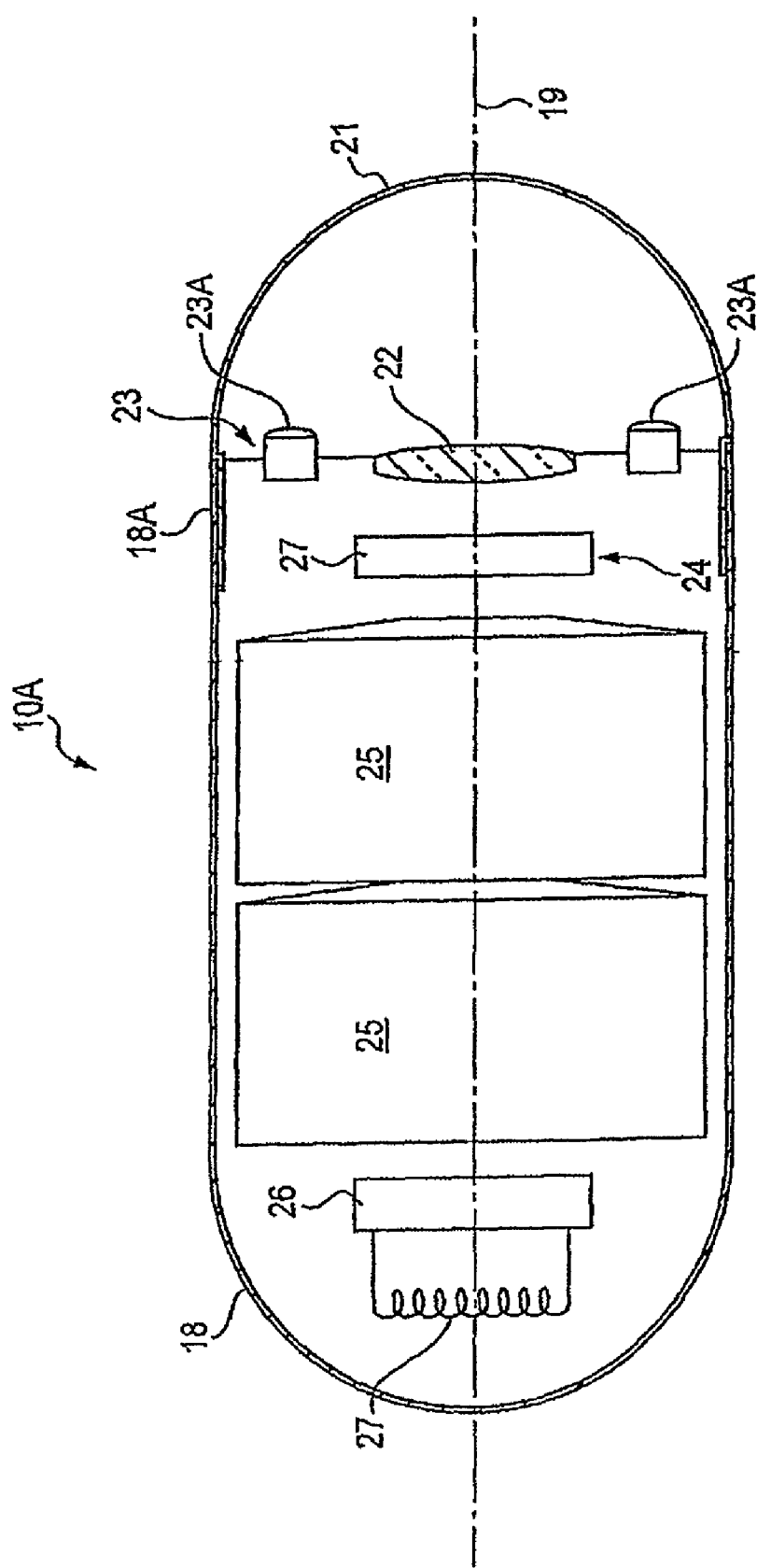
FIG. 1 is a schematic diagram illustrating an embodiment of a prior art autonomous in-vivo imaging device.

The remaining surface portion 30B of the CMOS imager 30, may include, inter alia, integrated circuitry (not shown in detail) for performing various control and timing functions, analog to digital (A/D) conversion circuitry (not shown) for converting the analog signal sampled from the individual pixels and various input/output (I/O) circuitry (not shown in detail for sending the image digitized data and control signals as output signals to devices or circuitry (not shown) such as but not limited to a transmitter like the transmitter 26 of FIG. 1, or any other signal processing circuit or element or unit which may be connected to the CMOS imager 30, as is known in the art.

Reference is now made to FIG. 3 which is a schematic front view of the imager 24 of FIG. 1. The imager 24 of FIG. 1 may be a CMOS imager and may be configured to have a square shape having a side length S (as seen in the front view of FIG. 3).

The CMOS imager 24 may include an imaging sensor part 24A which is may be typically located at the center of the frontal surface of the CMOS imager 24. The imaging sensor part 24A may include the two dimensional array of light sensitive diodes (not shown in detail) comprising the sensor pixels (not shown in detail), and may also include integrated amplification circuitry (not shown) and switching circuitry (not shown) for controlling the pixel sampling or readout, and may also include electrical conducting paths for connecting the pixels to the functional units that perform the readout of the pixels.

The remaining surface portion 24B of the of the CMOS imager 24, which surrounds the imaging sensor part 24A, may include, inter alia, integrated circuitry (not shown in detail for performing various control and timing functions, analog to digital (A/D) conversion circuitry (not shown) for converting the analog signal sampled from the individual pixels and various input/output (I/O) circuitry (not shown in detail) for sending the image digitized data and control signals as output signals to devices or circuitry (not shown) such as but not limited to a transmitter like the transmitter 26 of FIG. 1, or any other signal processing circuit or element or unit which may be connected to the CMOS imager 24.

The advantage of the imager configuration shown in FIG. 3, is that it makes possible to position the optical system 22 (best seen in FIG. 1) in the center of the optical window 21 (See FIG. 1) without unduly increasing the cross-sectional area of the entire device 10A of FIG. 1). However, with the configuration (shown in FIG. 3) of the CMOS imager 24, if it is desired to minimize the cross-sectional area of the device 10A, the diminishing of the cross-sectional area of the entire device IA may be limited by tee diagonal of the entire CMOS imager 24.

Reference is now made to FIG. 4 which is a schematic cross sectional view illustrating a CMOS imager having a square cross-sectional area disposed within a housing having a circular cross-section.

The CMOS imager 24 is shown disposed within a housing 28 having a wall 28A. The housing 28 has a circular cross-section. The wall 28A may be part of a capsule like housing, such as the housing 18 shown in the capsule-like device 10A of FIG. 1). The wall 28A may also be the wall of an imaging unit which comprises part of an elongated device such as a catheter-like device (not shown), or an endoscope-like device (not shown) or the like.

Similar to the CMOS imager 24 of FIG. 3, the square CMOS imager 34 of FIG. 4 may have a square imaging sensor part 34A (having a side length of $A_i$) including the imaging pixels (the pixels are not shown in detail) and a remaining surface part 34B which surrounds the imaging sensor part 34A and which may include all the supporting circuitry (not shown) as disclosed in detail hereinabove for the surface part 24B of FIG. 3. The entire CMOS imager 34 has a side S, and diagonal D. It can be seen from FIG. 4 that the internal diameter of the wall 28A of the housing 28 may not be smaller than the length of the diagonal D of the square CMOS imager 34. Thus, using the configuration of the CMOS imager 34, it is not possible to decrease the diameter of the housing 28 to a length smaller than the diagonal D of the entire CMOS imager 34.

Reference is now made to FIG. 5 which is a schematic top view showing the layout of a rectangular CMOS imager having segregated pixel array area and support circuitry areas, in accordance with a preferred embodiment of the present invention. The CMOS imager 54 may include a square imaging sensor part 54A (having a side length of $A_i$) including the imaging pixels (the pixels are not shown in detail) and a remaining surface part 54B which is longitudinally segregated from the imaging sensor part 54A and which may include all the necessary supporting circuitry (not shown) as disclosed in detail hereinabove.

The length $L_i$ of the CMOS imager 54 is adapted such that all the necessary supporting circuitry may be accommodated in the part 54B. Thus, when the CMOS imager 54 is compared to the CMOS imager 34 of FIG. 4, the dimensions of the imaging sensor parts 34A and 54A are the same (both imaging sensor parts may be a square having a side length of $A_i$), the CMOS imager 34 has a square shape having a side $S_i$ while the CMOS imager 54 has an elongated shape having a length $L_i$.

Figure 6:
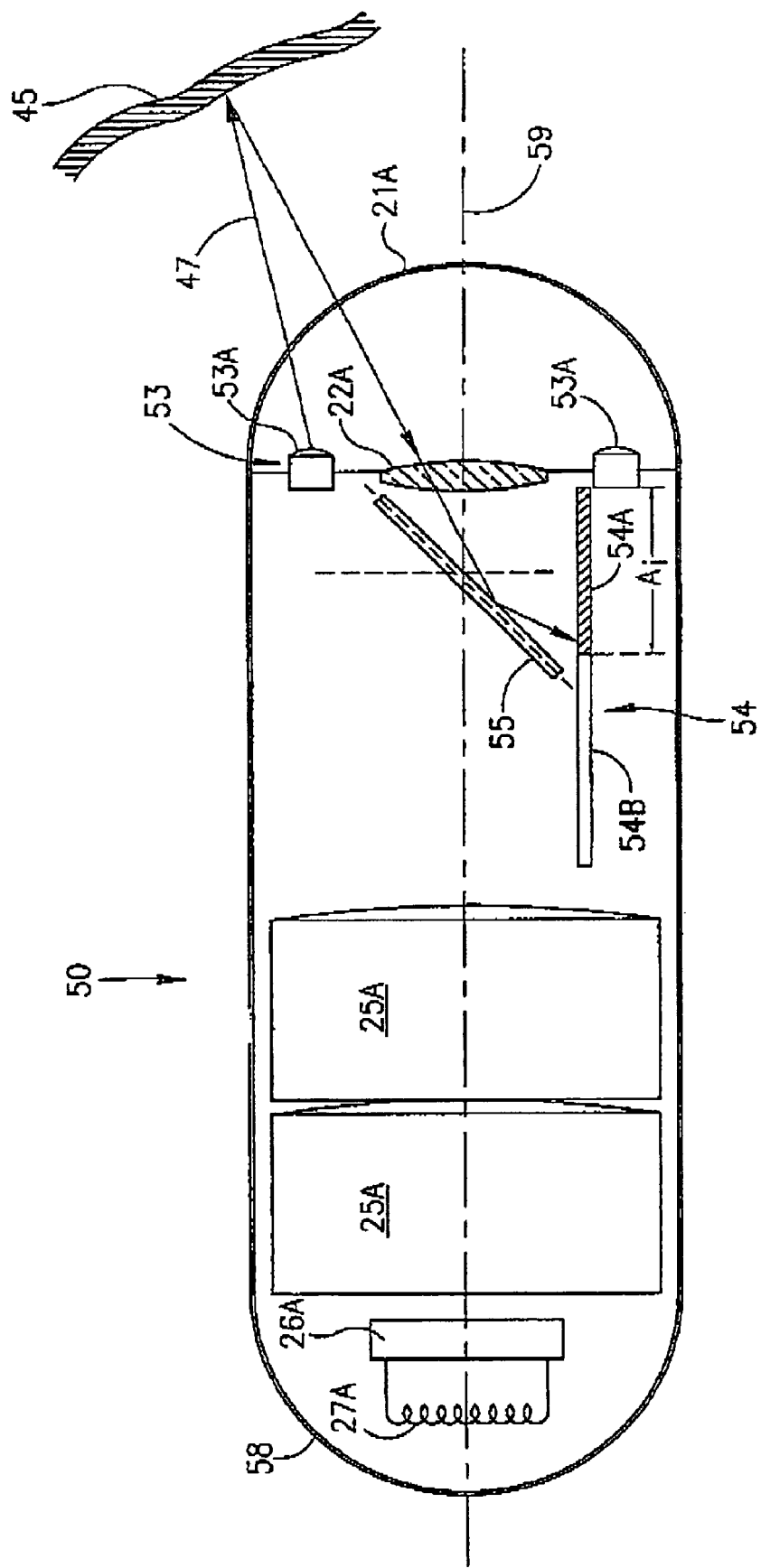
FIG. 6 is a cross sectional view illustrating an in-vivo imaging device having a reduced cross-sectional area and including the CMOS imager of FIG. 5, in accordance with a preferred embodiment of the present invention.

Reference is now made to FIG. 6 which is a cross-sectional view illustrating an in-vivo imaging device having a reduced cross-sectional area and including the CMOS imager of FIG. 5, in accordance with a preferred embodiment of the present invention.

The device 50 includes a capsule-like housing 58 which has an optical window 21A. The device 50 may include an optical system 22A and a mirror 55. The device 50 may include the CMOS imager 54 of FIG. 5. The mirror 55 may be substituted by any suitable light deflecting element such as a suitably configured prism, or the like, for deflecting the light rays collected by the 22A optical system towards the part 54A of the CMOS imager 54. The optical system 22A may be a lens, a group of lenses, a zoom lens, a composite lens, a wide angle lens or any other suitable image forming optical element known in the art.

The device 50 further includes the power sources 25A which may be similar to the power sources 25 of FIG. 1 but may be smaller in size due to the reduced cross sectional area of the device 50. The device 50 also includes an illuminating unit 53 comprising the light sources 53A. The construction and operation of the illuminating unit 53 and the light sources 53A may be as disclosed in detail for the illuminating unit 23 and the light sources 23A of FIG. 1, and possibly, as disclosed in WO 01/65995. The device 50 may also include a wireless transmitter 26A and an antenna 27A for transmitting the data of the acquired images.

The CMOS imager 54 is disposed longitudinally within the housing 58 such that the light rays 47 generated by the light sources 53A are reflected from the intestinal wall and pass through the optical window 21A. The reflected light rays are collected by the optical system 22A and are deflected towards the part 54A of the CMOS imager 54 to create an image to be sensed by the light sensing pixels (not shown) included in the part 54A. Preferably, but not necessarily, the CMOS imager 54 is disposed such that its longitudinal axis (not shown) is aligned parallel to the longitudinal axis 59 of the device 50. The angle α between the surface of the mirror 55 and the surface of the CMOS imager may be 45°, but may also be smaller than 45°. If the angle α is smaller than 45°, the image projected upon the pixels of the part 54A of the CMOS imager 54 may be distorted. Thus, the optical system 22A may be configured to suitably change the collected image in order to compensate for the distortion before the image reaches the part 54A of the CMOS imager 54. Alternatively, the distortion in the acquired image may be corrected after the acquisition by suitably processing the image data at a stage later than image acquisition. For example a distorted image may be processed in a workstation (not shown) after the image has been transmitted by the transmitter 26A. Such a distortion may be compensated by suitable computational algorithms, as is known in the art.

It is noted that in comparison to the configuration of the CMOS imaging unit 24 of FIG. 1 and the CMOS imaging unit 34 of FIG. 4 which are oriented perpendicular the longitudinal axis of the in vivo imaging device 10A, the configuration of the CMOS imager 54 being longitudinal and parallel to the axis 59 of the device 50 may enable a substantial reduction in the cross sectional area of the device 50 since the combination of the reduced area of the tight sensitive part 54A and the use of the mirror 55 allow such a reduction in cross-sectional area. It is noted that the cross sectional area $(Ai)^2$ of the part 54A of FIG. 6 is substantially smaller than the cross sectional area $(D)2$ of the entire CMOS imager 34 of FIG. 4. The cross-sectional area of a cross section taken in a direction perpendicular to the longitudinal axis the device 50 may therefore be substantially reduced in comparison to the cross sectional area of a cross section taken in a direction perpendicular to the longitudinal axis 19 of the device 10A.

It is noted that additional configurations of the optical components of the in vivo imaging device may be possible.

Figure 7:
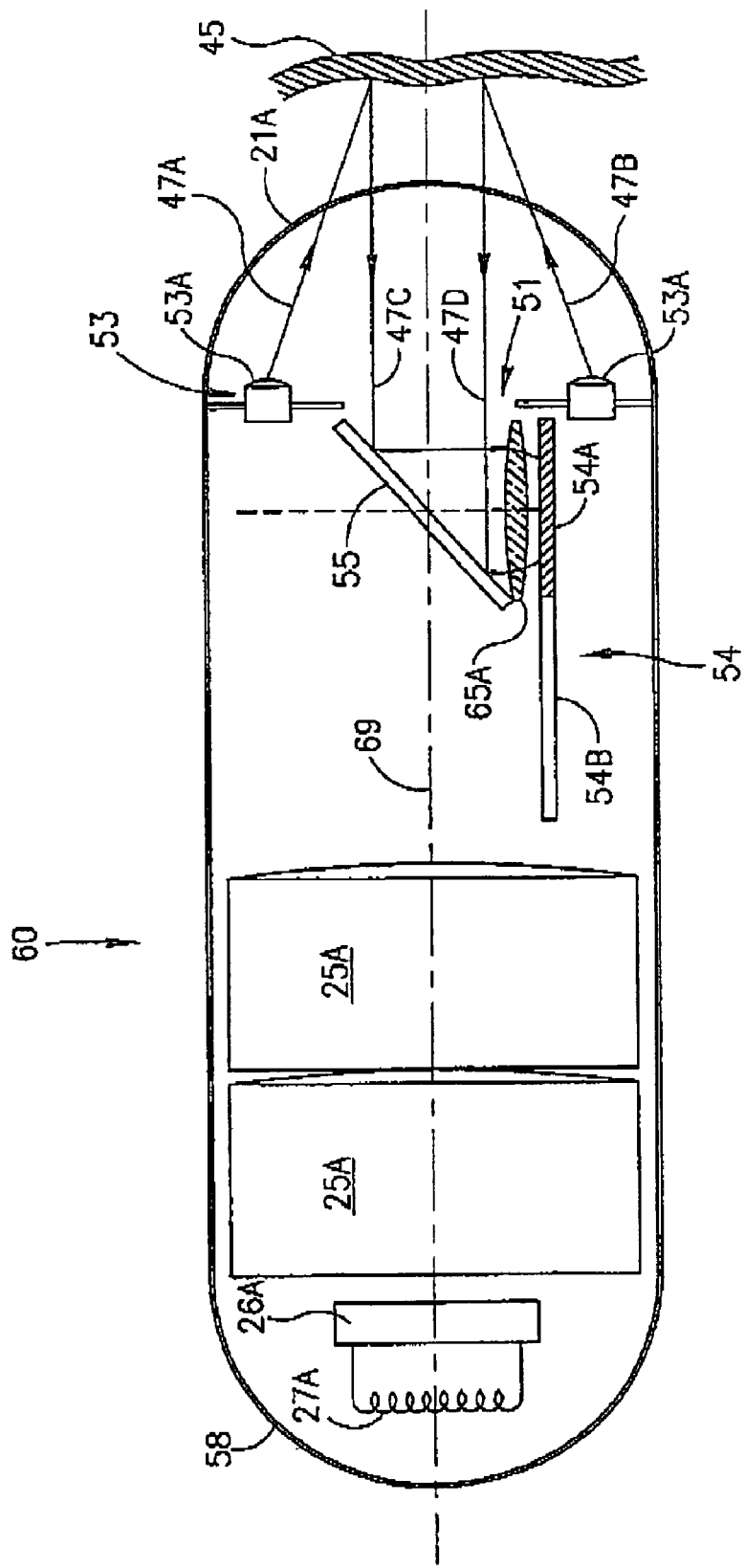
FIG. 7 is a cross-sectional view illustrating an in-vivo imaging device having a reduced cross-sectional area and including the CMOS imager of FIG. 5, in accordance with another preferred embodiment of the present invention.

Reference is now made to FIG. 7 which is a cross-sectional view illustrating an in-vivo imaging device having a reduced cross-sectional area and including the CMOS imager of FIG. 5, in accordance with another preferred embodiment of the present invention.

The device 60 includes a capsule-like housing 58 which has an optical window 21A. The device 60 may include an aperture 51, an optical system 65A and a mirror 55. The device 60 may include the CMOS imager 54 of FIG. 6. The mirror 55 may be substituted by any suitable light deflecting element such as a suitably configured prism (not shown), or the like, for deflecting the light rays 47C passing through by the aperture 51, towards the optical system 65A which projects an image on the part 54A of the CMOS imager 54. The optical system 65A may be a lens, a group of lenses, a zoom lens, a composite lens, a wide angle lens or any other suitable image forming optical element known in the art.

The device 60 further includes the power sources 25A which may be similar to the power sources 25A of FIG. 6.

The CMOS imager 54 is disposed longitudinally within the housing 68 such that the light rays 47A and 47B generated by the light sources 53A are reflected from the intestinal wall 45 and pass through the optical window 21A as tight rays 47C and 47D, respectively. The reflected light rays 47C and 47D are deflected by the mirror 55 towards the optical system 22A. The optical system 65A thus focuses an image on the part 54A of the CMOS imager 54 the image may be sensed by the light sensing pixels (not shown) included in the part 54A. Preferably, but not necessarily, the CMOS imager 54 is disposed such that its longitudinal axis (not shown) is aligned parallel to the longitudinal axis 69 of the device 60. The angle α between the surface of the mirror 55 and the surface of the CMOS imager may be 45°, but may also be smaller than 45°.

If the angle α is smaller than 45°, the image projected upon the pixels of the part 54A of the CMOS imager 54 may be distorted. Thus, the optical system 65A may be configured to suitably change the collected image in order to compensate for the distortion before the image reaches the part 54A of the CMOS imager 54. Alternatively, the distortion in the acquired image may be corrected after the acquisition by suitably processing the Image data at a stage later than image acquisition. For example, a distorted image may be processed in a workstation (not shown) after the image has been transmitted by the transmitter 26A. Such a distortion may be compensated by suitable computational algorithms, as is known in the art.

The configuration of the imager 54 and the mirror 55 and the optical system 65A of the device 60 may also enable the device 60 to have a reduced cross sectional area for the reasons disclosed in detail hereinabove.

Thus, the combination of the CMOS imager having segregated imaging and support circuitry parts disclosed hereinabove, and the longitudinal arrangement of such a segregated CMOS imager within the device allow the construction of autonomous or non-autonomous in vivo imaging devices with a small cross sectional area. The non-autonomous devices may include but are not limited to imaging heads or imaging units or imaging assemblies which are constructed as an integral part of, or are included within, or are attached to catheter like devices, endoscope-like devices, trocars, or any other type of device which may be used for in vivo surgical and/or diagnostic purposes requiring imaging capabilities and may benefit from the reduced cross-sectional area of such imaging heads or imaging units or imaging assemblies.

Figure 8:
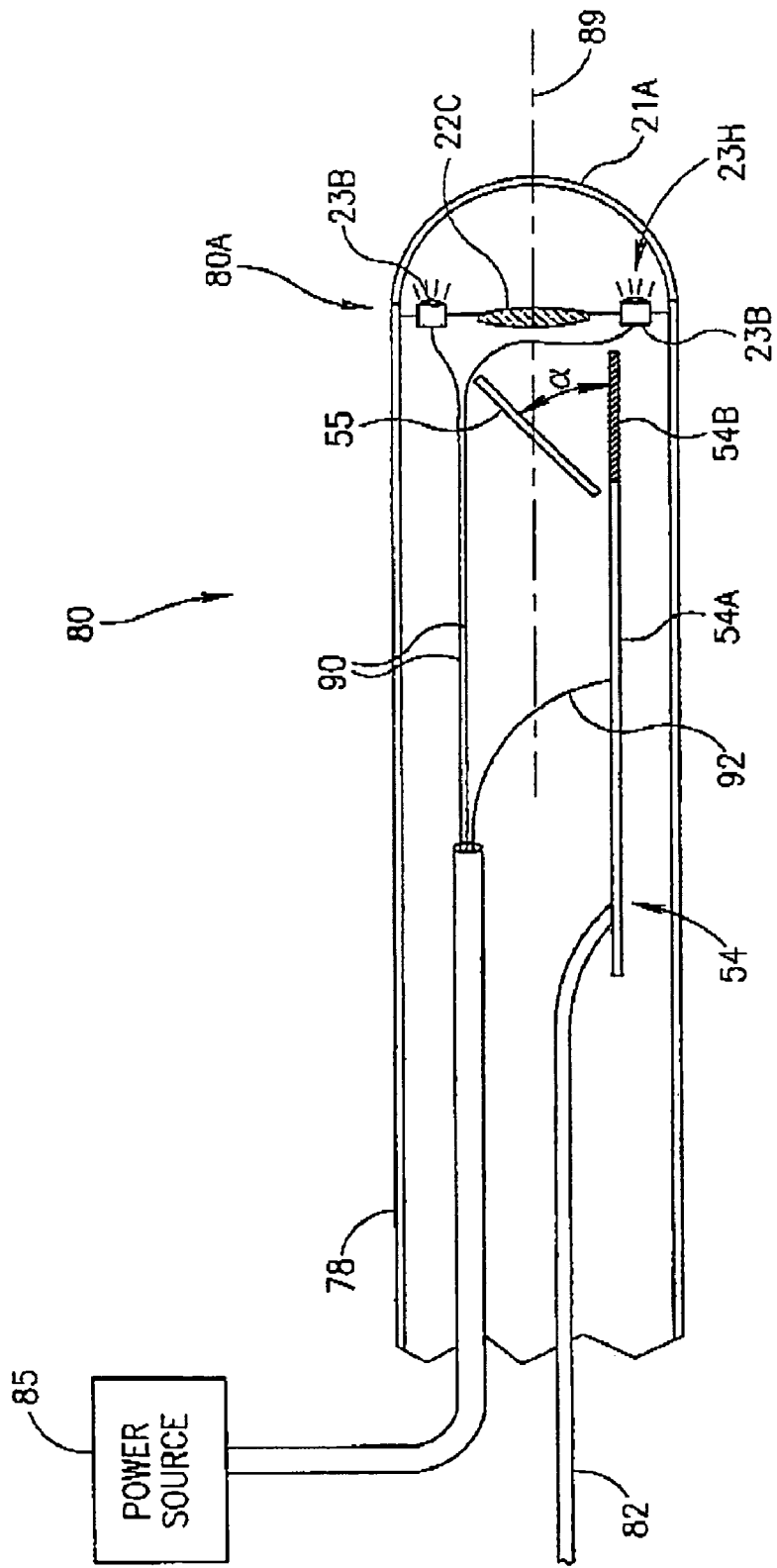
FIG. 8 is a schematic cross sectional view of part of an insertable device for in vivo imaging, in accordance with a preferred embodiment of the present invention.

Reference is now made to FIG. 8 which is a schematic cross sectional view of part of an insertable device for in vivo imaging, in accordance with a preferred embodiment of the present invention.

The insertable device 80 may include an elongated (preferably flexible) housing 78. The housing 78 may have an optical window 21A sealingly attached at the end 80A thereof. The device 80 may further include the CMOS imager 54 which is arranged longitudinally within the housing 78. The CMOS imager 54 has an imaging light sensitive part 54A segregated from other support circuitry part 54B as disclosed in detail hereinabove with respect to FIGS. 5-7.

The device 80 may include a mirror 55 which is inclined at an angle α to the imaging part 54A of the CMOS imager 54, as disclosed hereinabove. The angle α may be equal to 45° or may be different than 45°. Making the angle α smaller than 45°, may enable further reduction of the diameter or the cross sectional area of the device 80 as disclosed hereinabove for the devices 50 and 60. An optical system 22C may be suitably aligned along the longitudinal axis 89 of the device 80. The optical system 22C may include a single lens, multiple lenses, or other suitable optical elements like filters, as disclosed in detail hereinabove for me optical systems 22, 22A and 65A of FIGS. 1,6 and 7, respectively.

The device 80 may include an illumination unit 23H which may include light sources 23B. The light sources 23B may be the while LED light sources disclosed in detail hereinabove, and possibly, as disclosed in WO 01/15995., but may also be any other suitable miniature light sources known in the art. The CMOS imager 54 may be connected to a suitable power source 85 by suitable electrically conducting wires 92 connected to the power source 85. The CMOS imager 54 may be connected to suitable electrically conducting wires 82 for transmitting the image data to an external device (not shown) for further processing and for displaying of the acquired images.

It is noted that in accordance with another preferred embodiment of the present invention, the image data may be transmitted wirelessly to a receiver or a receiver/recorder, as is disclosed in detail for the autonomous in vivo imaging device 10A, and possibly, as disclosed in WO 01/65995. In such a case the device 80 may include an internal power source, a wireless transmitter (such as but not limited to the transmitters 26 or 26A of FIGS. 1, 6 and 7) and an antenna (such as but not limited to the antenna 27 of the device 10A).

The light sources 23B may be connected to the power source 85 by suitable electrically conducting wires 90 disposed within the housing 78. Alternatively, the light sources 23B may receive power and may be controlled by being coupled to the CMOS imager 54 (connections are not shown).

The power source 85 may be any suitable electrical power source, including but not limited to a mains operated power source, a battery, or the like. Alternatively, the power source 85 may be disposed within the housing 78 (not shown).

Other alternative designs of the optical arrangement in the device 80 may also be used. For example, the device 80 may have an optical aperture (such as, for example, the optical aperture 51 of FIG. 7) and an optical system (such as, for example, the optical system 65A of FIG. 7) disposed between the part 54A of the CMOS imager 54 and the mirror 55.

If the angle α is smaller than 45°, and a correction is needed for the distortion in the image, the distortion may be corrected by the optical system 22C (or by the optical system disposed between the part 54A of the CMOS imager 54 and the mirror 55, if the alternative optical arrangement is being used). Alternatively, image distortion may be corrected computationally by suitably processing the image data in a post-acquisition step, as is known in the art.

The segregated circuitry design of the CMOS imager 54 and the use of the mirror 55, enable the reduction of the transverse cross sectional area of the device 80 as explained in detail hereinabove for the devices 50 and 60 of FIGS. 6 and 7 respectively.

It is noted that, for the sake of simplicity of illustration, the insertable device 80 is illustrated as having imaging capabilities only. The device 80 may for example be inserted into a working channel of an endoscope (not shown) and may be used for insertion into and imaging of narrow cavities into which the endoscope cannot be inserted. However, The device 80 itself may include one or more working channels (not shown in FIG. 8 for the sake of clarity of illustration). The working channels may be used for performing insufflation and/or irrigation as is known in the art. Additionally, one or more instruments may be inserted into such working channels for performing a variety of surgical operations. Such instruments may includes but are not limited to scissors, other surgical blades, wire snares, banding devices, surgical laser devices, cauterizers, or any other surgical or diagnostic instrument known in the art and insertable through such a working channel. Thus, if the device 80 includes one or more working channels, the device 80 may be operated as an endoscopy device as is known in the art.

While the invention has been described with respect to a limited number of embodiments, it will be appreciated that many variations, modifications and other applications of the invention may be made which are within the scope and spirit of the invention.

The invention claimed is:

1. An in vivo imaging device, comprising:
   a capsule shaped housing having a longitudinal axis and an optical window at an end of the housing;
   a CMOS image sensor comprising a pixel array portion and a circuitry portion, wherein said pixel array portion is disposed within said housing substantially parallel to said longitudinal axis;
   a light deflecting element for deflecting received light to said pixel array portion, wherein the angle between said light deflecting element and said pixel array portion is smaller than 45° thereby distorting an image projected onto said pixel array portion; and
   a mechanism to compensate for said distortion.

2. The device of claim 1 wherein the pixel array portion is continuous with the circuitry portion.

3. The device of claim 1 wherein the circuitry portion comprises circuitry selected from the group consisting of timing circuitry, analog to digital conversion circuitry, input/output (I/O) circuitry, transmitting circuitry or a combination thereof.

4. The device of claim 1, wherein the light deflecting element is a mirror.

5. The device of claim 1, wherein said mechanism to compensate for said distortion includes an optical system configured to change an image to compensate for distortion of an image by the light deflecting element before the image reaches said pixel array portion.

6. The device of claim 5, wherein said optical system comprises a lens within said housing, configured to collect light rays coming through said optical window.

7. The device of claim 1 further comprising an aperture for reflected light to progress through.

8. The device of claim 1,further comprising a plurality of light emitting devices.

9. The device of claim 1, wherein said mechanism to compensate for said distortion comprises a workstation for processing distorted image data after acquisition.

10. The device of claim 1, comprising an optical system, wherein the optical system is substantially parallel to said longitudinal axis.

11. The device of claim 1, comprising an optical system, wherein the optical system is disposed between the image sensor and the light deflecting element.

* * * * *